United States Patent
Koslow

(10) Patent No.: US 8,613,363 B2
(45) Date of Patent: *Dec. 24, 2013

(54) INTEGRATED PAPER COMPRISING FIBRILLATED FIBERS AND ACTIVE AGENTS IMMOBILIZED THEREIN

(75) Inventor: Evan E. Koslow, Weston, CT (US)

(73) Assignee: KX Technologies LLC, West Haven, CT (US)

( * ) Notice: Subject to any disclaimer, the term of this patent is extended or adjusted under 35 U.S.C. 154(b) by 526 days.

This patent is subject to a terminal disclaimer.

(21) Appl. No.: 12/607,665

(22) Filed: Oct. 28, 2009

(65) Prior Publication Data

US 2010/0044289 A1 Feb. 25, 2010

Related U.S. Application Data

(60) Division of application No. 10/666,878, filed on Sep. 19, 2003, now Pat. No. 7,655,112, which is a continuation-in-part of application No. 10/622,882, filed on Jul. 18, 2003, now Pat. No. 7,296,691, and a continuation-in-part of application No. 10/286,695, filed on Nov. 1, 2002, now Pat. No. 6,835,311.

(60) Provisional application No. 60/354,062, filed on Jan. 31, 2002.

(51) Int. Cl.
*B01D 39/18* (2006.01)
*B01D 39/08* (2006.01)
*B01D 39/02* (2006.01)
*C02F 1/68* (2006.01)

(52) U.S. Cl.
USPC ........... 210/501; 210/505; 210/508; 210/694; 210/764; 162/181.9; 162/23; 162/157.6

(58) Field of Classification Search
None
See application file for complete search history.

(56) References Cited

U.S. PATENT DOCUMENTS

| | | | |
|---|---|---|---|
| 3,019,127 A | 1/1962 | Czerwonka et al. | |
| 3,268,444 A * | 8/1966 | Renn | 210/679 |
| 4,416,698 A | 11/1983 | McCorsley, III | |
| 4,459,332 A | 7/1984 | Giglia | |
| 4,495,030 A | 1/1985 | Giglia | |
| 4,565,727 A | 1/1986 | Giglia et al. | |
| 4,648,902 A | 3/1987 | Giglia | |
| 4,793,837 A | 12/1988 | Pontius | |
| 4,859,340 A | 8/1989 | Hou et al. | |
| 4,904,343 A | 2/1990 | Giglia et al. | |
| 4,929,502 A | 5/1990 | Giglia | |
| 4,963,431 A | 10/1990 | Goldstein et al. | |
| 5,019,311 A | 5/1991 | Koslow | |
| 5,161,686 A | 11/1992 | Weber et al. | |
| 5,180,630 A | 1/1993 | Giglia | |
| 5,192,604 A | 3/1993 | Giglia | |
| 5,415,779 A | 5/1995 | Markell et al. | |
| 5,595,649 A | 1/1997 | Markell et al. | |
| 5,671,757 A | 9/1997 | Woodings | |
| 5,681,468 A | 10/1997 | Sawan et al. | |
| 5,817,325 A | 10/1998 | Sawan et al. | |
| 5,888,526 A | 3/1999 | Tsubai et al. | |
| 6,155,432 A | 12/2000 | Wilson et al. | |
| 6,231,657 B1 | 5/2001 | Cantiani et al. | |
| 6,267,898 B1 | 7/2001 | Fukuda et al. | |
| 6,402,951 B1 | 6/2002 | Wilson et al. | |
| 6,406,594 B1 | 6/2002 | Palmer et al. | |
| 6,479,150 B1 | 11/2002 | Liu et al. | |
| 6,554,881 B1 | 4/2003 | Healey | |
| 6,602,994 B1 | 8/2003 | Cash et al. | |
| 6,630,016 B2 | 10/2003 | Koslow | |
| 6,673,136 B2 | 1/2004 | Gillingham et al. | |
| 6,835,311 B2 | 12/2004 | Koslow | |
| 6,953,604 B2 | 10/2005 | Koslow | |
| 6,959,820 B2 | 11/2005 | Koslow | |
| 6,998,058 B2 | 2/2006 | Koslow | |
| 7,011,753 B2 | 3/2006 | Koslow | |
| 7,144,533 B2 | 12/2006 | Koslow | |
| 2001/0004869 A1 | 6/2001 | Cantiani et al. | |
| 2002/0022012 A1* | 2/2002 | Cooper et al. | 424/78.17 |
| 2002/0173213 A1 | 11/2002 | Chu et al. | |
| 2003/0037675 A1 | 2/2003 | Gillingham et al. | |
| 2003/0127393 A1 | 7/2003 | Tepper et al. | |
| 2003/0141261 A1 | 7/2003 | Koslow | |
| 2003/0168401 A1 | 9/2003 | Koslow | |
| 2003/0177909 A1 | 9/2003 | Koslow | |
| 2003/0196963 A1 | 10/2003 | Koslow | |
| 2003/0196964 A1 | 10/2003 | Koslow | |
| 2003/0201231 A1 | 10/2003 | Koslow | |
| 2003/0205529 A1 | 11/2003 | Koslow | |

(Continued)

FOREIGN PATENT DOCUMENTS

| | | |
|---|---|---|
| EP | 145849 A1 | 6/1985 |
| EP | 199150 A1 | 10/1986 |
| EP | 265762 A1 | 5/1988 |
| GB | 2325248 | 5/1997 |
| WO | 03/064006 | 8/2003 |
| WO | WO 2005018769 A2 | 3/2005 |

OTHER PUBLICATIONS

Celanese Acetate, "Complete Textile Glossary" 2002, Celanese Acetate LLC, pp. 97.

*Primary Examiner* — Krishnan S Menon

(74) *Attorney, Agent, or Firm* — Robert Curcio; DeLio & Peterson, LLC

(57) ABSTRACT

Disclosed is an integrated paper wherein the paper has capabilities and functionalities provided by both the fiber and the active agent ingredients, and a method of immobilizing the active agents within the integrated paper. The tight pore structure of the integrated paper of the present invention, a mean pore diameter of less than about 2 microns, provides short diffusion distances from a fluid to the surface of the paper ingredients by adsorption or diffusive interception making it an excellent medium for fluid filtration. The integrated paper of the present invention can further include a microbiological interception enhancing agent. The integrated paper can be formed using, preferably, wet laid paper-making processes for speed and efficiency. Also disclosed are devices utilizing the integrated paper useful in fluid filtration.

25 Claims, No Drawings

(56) References Cited

U.S. PATENT DOCUMENTS

| | | |
|---|---|---|
| 2003/0205530 A1 | 11/2003 | Koslow |
| 2003/0205531 A1 | 11/2003 | Koslow |
| 2003/0213750 A1 | 11/2003 | Koslow |
| 2004/0031749 A1 | 2/2004 | Koslow |
| 2004/0084378 A1 | 5/2004 | Koslow |
| 2004/0163782 A1 | 8/2004 | Hernandez-Munoa et al. |
| 2004/0178142 A1 | 9/2004 | Koslow |
| 2004/0191470 A1 | 9/2004 | Zafiroglu et al. |
| 2005/0023211 A1 | 2/2005 | Koslow |
| 2005/0051487 A1 | 3/2005 | Koslow |
| 2007/0224419 A1 | 9/2007 | Sumnicht et al. |
| 2007/0248819 A1 | 10/2007 | Manner et al. |
| 2007/0298064 A1 | 12/2007 | Koslow |
| 2008/0116125 A1 | 5/2008 | Nero et al. |
| 2009/0020248 A1 | 1/2009 | Sumnicht et al. |
| 2009/0084513 A1 | 4/2009 | Barnholtz et al. |

* cited by examiner

INTEGRATED PAPER COMPRISING FIBRILLATED FIBERS AND ACTIVE AGENTS IMMOBILIZED THEREIN

This is a divisional application of U.S. patent application Ser. No. 10/666,878, now U.S. Pat. No. 7,655,112, filed on Sep. 19, 2003, which is a continuation-in-part of U.S. patent application Ser. No. 10/622,882, now U.S. Pat. No. 7,296,691, filed on Jul. 18, 2003 and of U.S. patent application Ser. No. 10/286,695, now U.S. Pat. No. 6,835,311, filed on Nov. 1, 2002, which claims priority from U.S. Provisional Application Ser. No. 60/354,062 filed on Jan. 31, 2002.

The present invention is directed to an integrated paper made with nanofibers, the integrated paper having particles of active agents immobilized therein, filtration systems including same, and methods of making and using.

SUMMARY OF THE INVENTION

The present invention is directed to, in a first aspect, an integrated paper having active particles immobilized therein, the integrated paper comprising of: a plurality of fibers fibrillated at a temperature greater than about 30° C., wherein the fibrillated fibers have an average fiber diameter of less than about 1000 nm; and active agents comprising metals, metal salts, metal oxides, alumina, carbon, activated carbon, silicates, ceramics, zeolites, diatomaceous earth, activated bauxite, fuller's earth, calcium sulfate, titanium dioxide, magnesia, magnesium hydroxide, magnesium oxide, manganese oxides, iron oxides, perlite, talc, clay, bone char, calcium hydroxide, calcium salts, or combinations thereof, wherein the integrated paper has a mean pore size of less than or equal to about 2 μm.

The active agents can have different settling velocities such that the integrated paper has an asymmetric structure when formed by wet-laid processes.

Preferably, the integrated paper may further include a microbiological interception enhancing agent.

In another aspect, the present invention is directed to an integrated paper comprising of: a plurality of fibers fibrillated at a temperature greater than about 30° C., wherein the fibrillated fibers have an average fiber diameter of less than about 400 nm; and silver oxide particles admixed with the fibrillated fibers. Preferably, the fibrillated fibers comprise a liquid crystal polymer.

In yet another aspect, the present invention is directed to an integrated paper comprising of: a plurality of fibers fibrillated at a temperature greater than about 30° C., wherein the fibers have an average fiber diameter of less than about 400 nm; and one or more acid neutralizing agents admixed with the fibrillated fibers; wherein the integrated paper can withstand a hot and corrosive environment of a lube oil filter. The integrated paper may further include binder fiber particles. Preferably, the one or more acid neutralizing agents comprises magnesium oxide, magnesium hydroxide, calcium sulfonate, magnesium sulfonate, calcium phenate, magnesium phenate, or combinations thereof.

In still yet another aspect, the present invention is directed to an integrated paper comprising of: a plurality of lyocell fibers fibrillated at a temperature greater than about 30° C., wherein the fibrillated lyocell fibers have an average fiber diameter of less than or equal to about 400 nm; and activated carbon particles admixed with the fibrillated lyocell fibers, wherein the integrated paper has a mean flow path of less than about 2 μm. The integrated paper may further include a microbiological interception enhancing agent, heavy metal reducing agents such as, for example, zeolite or silicate particles, and/or an arsenic reducing agent such as, for example, particles of an oxide of manganese or iron.

In a further aspect, the present invention is directed to an integrated paper comprising of: a plurality of fibers having an average fiber diameter of less than about 1000 nm; and a lead reducing agent admixed with the plurality of fibers, wherein the integrated paper has a mean flow path of less than about 2 μm. The integrated paper may further include binder fiber particles. The integrated paper may be wrapped around a carbon block.

In still a further aspect, the present invention is directed to a water filtration device comprising of: a carbon block; and an integrated paper upstream of the carbon block, the integrated paper having a mean flow path of less than about 2 μm and comprising an admixture of: fibrillated fibers having an average fiber diameter of less than about 1000 nm; and active agents comprising metals, metal salts, metal oxides, alumina, carbon, activated carbon, silicates, ceramics, zeolites, diatomaceous earth, activated bauxite, fuller's earth, calcium sulfate, titanium dioxide, magnesia, magnesium hydroxide, magnesium oxide, manganese oxides, iron oxides, perlite, talc, clay, bone char, calcium hydroxide, calcium salts, or combinations thereof. Preferably, the integrated paper provides toxic material, heavy metal reduction, and/or a water softening effect. The integrated paper may further include a microbiological interception enhancing agent.

In still yet a further aspect, the present invention is directed to a gravity-flow water filtration device comprising of: a hydrophilic integrated paper having a mean flow path of less than about 2 μm comprising of: fibrillated fibers having an average fiber diameter of less than about 400 nm; and particles of activated carbon, heavy metal reducing agents, arsenic reducing agents, chemisorbent agents, or combinations thereof, wherein the gravity-flow water filtration device has a flow rate of about 10 to about 1000 ml/minute when operated at a pressure of about 4 inches water column. Preferably, the fibrillated fibers are fibrillated at a temperature of greater than about 30° C., and may comprise lyocell. Preferably, the average fiber diameter of the fibrillated fibers is smaller than an average particle size of the activated carbon, heavy metal reducing agents, and chemisorbent agents. The integrated paper may further include a microbiological interception enhancing agent.

In still yet a further aspect, the present invention is directed to a lube oil filtration device comprising of: an integrated paper in contact with the lube oil, the integrated paper comprising an admixture of: fibrillated fibers having an average fiber diameter of less than about 1000 nm; and an acid neutralizing agent. Preferably, the acid neutralizing agent comprises magnesium hydroxide or magnesium oxide.

In still yet a further aspect, the present invention is directed to an air treatment device for chemisorbing carbon dioxide, the device comprising of: an integrated paper comprising an admixture of fibrillated fibers having an average fiber diameter of less than about 1000 nm; and silver oxide, wherein the fiber diameter of the fibrillated fibers is smaller than an average particle size of the silver oxide.

In still yet a further aspect, the present invention is directed to method of immobilizing particles comprising of: providing a plurality of active agents comprising metals, metal salts, metal oxides, alumina, carbon, activated carbon, silicates, ceramics, zeolites, diatomaceous earth, activated bauxite, fuller's earth, calcium sulfate, titanium dioxide, magnesia, magnesium hydroxide, magnesium oxide, manganese oxides, iron oxides, perlite, talc, clay, bone char, calcium hydroxide, calcium salts, or combinations thereof; providing a plurality of fibers wherein at least a portion of the fibers have an average fiber diameter that is smaller than an average particle size of the active particles; admixing the active agents and the fibers; and forming an integrated paper having a mean flow path of less than about 2 μm with the admixture of active agents and fibers. Preferably, in the step of providing a plurality of fibers, the plurality of fibers are produced by fibrillation at temperatures of greater than about 30° C. Preferably, in the step of forming the paper, the paper is loaded with active particles up to about 95% by weight of the integrated paper.

DETAILED DESCRIPTION OF THE INVENTION

An integrated paper (meaning a paper with capabilities provided by both the fiber and particulate ingredients) of the present invention has a mean pore size of less than about 2.0 microns, preferably less than about 1 micron, that includes fibrillated nanofibers having a Canadian Standard Freeness of less than about 100, and an average fiber diameter of less than or equal to about 1000 nm, and active particles immobilized within the integrated paper. The tight pore structure of the integrated paper of the present invention provides short diffusion distances from affluid to the surface of the paper ingredients by adsorption or diffusive interception making it an excellent medium for fluid filtration. The integrated paper can be formed using, preferably, wet laid paper-making processes for speed and efficiency.

The active particles immobilized within the integrated paper can comprise metals, metal salts, metal oxides, alumina, carbon, activated carbon, silicates, ceramics, zeolites, diatomaceous earth, activated bauxite, fuller's earth, calcium sulfate, titanium dioxide, magnesia, magnesium hydroxide, magnesium oxide, manganese oxides, iron oxides, perlite, talc, clay, bone char, calcium hydroxide, calcium salts, or combinations thereof. The active particles provide a functionality to the integrated paper for applications such as, for example, adsorption of carbon dioxide with silver oxide in air filtration; controlling acidity in lube oil with magnesium oxide/hydroxide; combinations of activated carbon and a lead reducing agent, such as zeolites or amorphous titanium silicate as examples, to provide an inexpensive cyst-reducing water filtration medium that also intercepts lead, chlorine, taste, and odors; and immobilizing titanium dioxide for the production of photocatalytic membranes.

Furthermore, the fibrillated fibers, or nanofibers, alone or in combination with other ingredients of the integrated paper can be treated with a microbiological interception enhancing agent to impart anti-microbial activity to the integrated paper. Preferably, the microbiological interception enhancing agent utilizes a synergistic interaction between a cationic material and a biologically active metal, that when combined, provide broad-spectrum reduction of microbiological contaminants on contact. The charge provided by the cationic material to the integrated paper aids in electro-kinetic interception of microbiological contaminants, while the tight pore structure provides a short diffusion path and, therefore, rapid diffusion kinetics of contaminants in a flowing fluid to the surface of a surface of the paper. Due to the dominant role of diffusion for the interception of extremely small particles, there is a direct correlation between the reduction of contaminants, and the contact time of an influent within the integrated paper, rather than a simple dependence upon the thickness of the paper.

The Fibers

Fibers useful in making the integrated paper of the present invention are any fibers that can be fibrillated into nanofibers. The fibers preferably comprise organic polymeric fibers that are capable of being fibrillated. Fibrillated fibers are most preferred due to their exceptionally fine dimensions and potentially low cost. Such fibrillated fibers include, but are not limited to, polymers such as polyamide, acrylic, acrylonitrile, liquid crystal polymers such as VECTRAN®, and the like; ion-exchange resins; engineered resins; cellulose; rayon; ramie; wool; silk; glass; other fibrous materials; or combinations thereof. Combinations of organic and inorganic fibers and/or whiskers whether fibrillated or not, are contemplated and within the scope of the invention. For example, glass, ceramic, or metal fibers and polymeric fibers may be used together. Glass or metal fibers can provide additional wet strength to the integrated paper. In a most preferred embodiment, fibrillated lyocell fibers are used due to their exceptionally fine dimensions and potentially low cost.

Fibrillatable cellulose fibers can be made by direct dissolution and spinning of wood pulp in an organic solvent, such as an amine oxide, and are known as lyocell fibers. Lyocell fibers have the advantage of being produced in a consistent, uniform manner, thus yielding reproducible results, which may not be the case for, for example, natural cellulose fibers. Further, the fibrils of lyocell are often curled. The curls provide a significant amount of fiber entanglement. As an added advantage, the fibrillated lyocell fibers may be produced in large quantities using equipment of modest capital cost. It will be understood that fibers other than cellulose may be fibrillated to produce extremely fine fibrils, such as for example, synthetic fibers, in particular, acrylic or polyacrylonitrile (PAN) fibers, or other cellulosic materials.

When produced by a wet laid process from fibers such as cellulose or polymer fibers, such nanofibers should have a Canadian Standard Freeness of less than or equal to about 100, preferably less than or equal to about 45, and most preferably less than or equal to about 0. However, it should be recognized that in some cases, Canadian Standard Freeness is not an ideal measure of fiber size, as in the case of extremely stiff fibers such as those produced from liquid crystal polymers such as VECTRAN®. In these cases, the fiber size should be directly assayed using microscopy. Preferably, a significant portion of the nanofibers should have a diameter less than or equal to about 1000 nanometers, more preferably less than or equal to about 400 nanometers, and nanofibers less than or equal to about 250 nanometers in diameter are most preferred. The diameter of the nanofibers is preferably less than an average particle size of said active agents for physical entrapment of the active agents. It is preferable to chop the original fibers prior to fibrillation to a length of about 1 millimeter to about 8 millimeters, preferably about 2 millimeters to about 6 millimeters, and more preferably about 3 millimeters to about 4 millimeters, and to sustain this fiber length during the fibrillation process by avoiding excessive fiber cutting.

Active Agents for Increased Functionality/Reinforcement

One or more active agents either in particulate, fiber, whisker, or powder form may be admixed with the nanofibers to provide added functionality and/or reinforcement to the integrated paper. Useful active agents may include, but are not limited to, metals, metal salts, metal oxides, alumina, carbon, activated carbon, silicates, ceramics, zeolites, diatomaceous earth, activated bauxite, fuller's earth, calcium sulfate, titanium dioxide, magnesia, magnesium hydroxide, manganese oxides, iron oxidess, perlite, talc, clay, bone char, calcium hydroxide, calcium salts, or combinations thereof. Such active agents can aid in the adsorption of contaminants such as heavy metals or volatile organic compounds (VOCs). The active agents can also be chemically treated to impart microbiological interception capabilities depending upon the particular application.

Different types of active agents can impart functionality to the integrated paper. Not intending to be bound by these or any examples disclosed herein, some applications where an integrated paper is particularly low cost and useful include, but are not limited to, an integrated paper with silver oxide for chemisorbing carbon dioxide in closed systems. The silver oxide, upon chemisorption of the carbon dioxide, forms silver carbonate. Upon exposure to heat, the silver carbonate reverts back to silver oxide and the integrated paper can be subject to addition chemisorption of carbon dioxide.

Filtration of industrial oils can be accomplished by filtering the oil through a filter medium comprising an integrated paper having immobilized therein additives that can boost the performance of the oil. For example only, the acidity of lubrication oil can be controlled by filtering the oil with an integrated paper containing acid neutralizing agents such as, for example, magnesium oxide or magnesium hydroxide. Preferably, in order to withstand the high working temperatures of industrial oil, the integrated paper is made with a synthetic fiber such as a liquid crystal polymer.

Other active agents include activated carbon, alone or in combination with a lead reducing agent, such as a titanium zeolite or amorphous silicate as examples. Such a zeolite-loaded integrated paper can also contain activated carbon and can be manufactured with a pore structure suitable for the direct interception of microbiological threats such as protozoan cysts, bacteria, or viral particles. Such an integrated paper can provide inexpensive cyst-reducing capabilities with lead, chlorine, taste, and odor reduction. The zeolite integrated paper can provide a water-softening effect by direct ion-exchange. Incorporating iron oxides or manganese oxides into the integrated paper, alone or in combination with other active agents, further provides arsenic reduction capability desirable in a water filtration medium. These papers can be used in conjunction with carbon block filtration media to boost performance of the entire filter system for little additional cost.

Integrated papers having immobilizing titanium dioxide therein are useful in photocatalytic processes, and are inexpensive and easy to manufacture using paper making processes.

The active agents are preferably present in a sufficient amount such that the fluid flow through the integrated paper is not substantially impeded when used as a filter medium. The amount of active agents is also dependent upon the particular use of the filtration system. Preferably, the active agents are present in an amount of up to about 50 weight percent based on a total weight of the integrated paper, and more preferably up to about 75 weight percent. Higher concentrations of active agents, such as up to about 95 weight percent, are contemplated and within the scope of the invention. The particle size of the active agents can be about 1 to about 5000 µm. As the size of the active agents decrease, higher loading rates of the active agents in the paper can be obtained.

One or more active agents can be chosen wherein particles of the one or more active agents have different settling velocities during production of the integrated paper. The resultant paper would have one or more particles settling to one surface of the paper and the fibers settling to the other surface such that an asymmetric pore gradient exists through the thickness of the paper. This asymmetry can produce a gradient in the pore structure from a prefiltration structure to a final polishing filter. For example, activated carbon particles can be admixed with nanofibers having a different density and settling velocity than the activated carbon particles such that under gravity conditions during initial paper formation form a gradient with a zone of nanofibers leading into a zone of activated carbon particles. An influent contacting an integrated paper of this type would be stripped of chemical impurities when first contacted with the activated carbon and followed by removal of particulate impurities when in contact with the nanofibers.

The strength of the integrated paper, especially when wet, may be improved with the addition of various active agents that can be reinforcing additives or binders. It is well known in the art that the addition of epoxy or acrylic or other resins to the paper making process can provide enhanced wet strength, but these water-dispersed resins often cause lower permeability to the final product, especially as fiber size becomes very small. Although these resins and resin systems can be used in the current invention, it is preferable to use thermoplastic or thermoset materials known in the art, and in either liquid, powder, particulate or fiber form.

Useful binders include, but are not limited to, polyolefins, polyvinyl halides, polyvinyl esters, polyvinyl ethers, polyvinyl sulfates, polyvinyl phosphates, polyvinyl amines, polyamides, polyimides, polyoxidiazoles, polytriazols, polycarbodiimides, polysulfones, polycarbonates, polyethers, polyarylene oxides, polyesters, polyarylates, phenol-formaldehyde resins, melamine-formaldehyde resins, formaldehyde-ureas, ethyl-vinyl acetate copolymers, co-polymers and block interpolymers thereof, and combinations thereof. Variations of the above materials and other useful polymers include the substitution of groups such as hydroxyl, halogen, lower alkyl groups, lower alkoxy groups, monocyclic aryl groups, and the like. Other potentially applicable materials include polymers such as polystyrenes and acrylonitrile-styrene copolymers, styrene-butadiene copolymers, and other non-crystalline or amorphous polymers and structures.

A more detailed list of binders that may be useful in the present invention include end-capped polyacetals, such as poly(oxymethylene) or polyformaldehyde, poly(trichloroacetaldehyde), poly(n-valeraldehyde), poly(acetaldehyde), and poly(propionaldehyde); acrylic polymers, such as polyacrylamide, poly(acrylic acid), poly(methacrylic acid), poly(ethyl acrylate), and poly(methyl methacrylate); fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), and poly(vinyl fluoride); polyamides, such as poly(6-aminocaproic acid) or poly(e-caprolactam), poly(hexamethylene adipamide), poly(hexamethylene sebacamide), and poly(11-aminoundecanoic acid); polyaramides, such as poly(imino-1,3-phenyleneiminoisophthaloyl) or poly(m-phenylene isophthalamide); parylenes, such as poly-2-xylylene, and poly(chloro-1-xylylene); polyaryl ethers, such as poly(oxy-2,6-dimethyl-1,4-phenylene) or poly(p-phenylene oxide); polyaryl sulfones, such as poly(oxy-1,4-phenylenesulfonyl-1,4-phenyleneoxy-1,4-phenyl-eneisopropylidene-1,4-phenylene), and poly(sulfonyl-1,4-phenylene-oxy-1,4-phenylenesulfonyl4,4'-biphenylene); polycarbonates, such as poly-(bisphenol A) or poly(carbonyldioxy-1,4-phenyleneisopropylidene-1,4-phenylene); polyesters, such as poly(ethylene terephthalate), poly(tetramethylene terephthalate), and poly(cyclohexyl-ene-1,4-dimethylene terephthalate) or poly(oxymethylene-1,4-cyclohexylenemethyleneoxyterephthaloyl); polyaryl sulfides, such as poly(p-phenylene sulfide) or poly(thio-1,4-phenylene); polyimides, such as poly(pyromellitimido-1,4-phenylene); polyolefins, such as polyethylene, polypropylene, poly(1-butene), poly(2-butene), poly(1-pentene), poly(2-pentene), poly(3-methyl-1-pentene), and poly(4-methyl-1-pentene); vinyl polymers, such as poly(vinyl acetate), poly(vinylidene chloride), and poly(vinyl chloride); diene polymers, such as 1,2-poly-1,3- butadiene, 1,4-poly-1,3-butadiene, polyisoprene, and polychloroprene; polystyrenes; and copolymers of the foregoing, such as acrylonitrilebutadiene-styrene (ABS) copolymers. Polyolefins that may be useful include polyethylene, linear low density polyethylene, polypropylene, poly(1-butene), poly(2-butene), poly(1-pentene), poly(2-pentene), poly(3-methyl-1-pentene), poly(4-methyl-1-pentene), and the like.

A range of binder fibers, including polyethylene, polypropylene, acrylic, or polyester-polypropylene or polypropylene-polyethylene bi-component fibers, or others can be used. Certain types of treated polyethylene fibers, when properly treated, as described below, are optimal, and have the additional benefit of not significantly interfering with the hydrophilic nature of the resulting filter medium when used in modest volumes. Preferred fiber binder materials may include FYBREL® synthetic fibers and/or SHORT STUFF® EST-8, both of which are polyolefin based. FYBREL® is a polyolefin based synthetic pulp that is a highly fibrillated fiber and is commercially available from Mitsui Chemical Company, Japan. FYBREL® has excellent thermal moldability and provides a smooth surface to the filter medium. SHORT STUFF® EST-8 is commercially available from MiniFibers, Inc., Pittsburgh, Pa., and is a highly fibrillated, high density polyethylene.

Preferably, one or more binders are present in an amount of about 1% to about 10% by weight, more preferably about 3% to about 6%, and most preferably about 5%. It is preferable that the binder material have a softening point that is significantly lower than a softening point of the nanofiber material so that the filter medium can be heated to activate the binder material, while the integrated paper does not melt and thereby lose porosity.

As the size of the active agents decrease, high loading rates of the active agents in the paper can be obtained. Preferably, the diameter of the binder fibers is equal to or less than the particle size of the active agents to effectively immobilize the active agents within the paper. Alternatively, in a binder-less paper, the diameter of the nanofibers is preferably equal to or less than the particle size of the active agents to effectively immobilize the active agents in the paper by physical entrapment. The smaller the particles of active agents are, the greater the diffusion kinetics for more effective interception of contaminants that are smaller than the mean flow path diameter.

The Integrated Paper as an Anti-Microbial Filter Medium

The tight pore structure of the integrated paper provides a short diffusion path and, therefore, rapid diffusion kinetics of microbiological contaminants in a flowing fluid to the surface of the integrated paper. The tight pore structure also provides supplemental direct mechanical interception of microbiological contaminants. The mean pore size of the integrated paper is less than about 2 microns, preferably less than about 1 micron, and can be less than about 0.5 microns. Thus, it would be advantageous to treat the fibers and/or active agents to impart anti-microbial properties to the integrated paper to further enhance microbiological contaminant removal.

The nanofibers and/or active agents, or the integrated paper itself, can be chemically treated with any compatible microbiological interception enhancing agent known in the art, with or without a biologically active metal. Examples of suitable anti-microbial agents include, without limitation, any bactericidal agent, bacteriostatic agent, fungicidal agent, fungistatic agent, or the like, that are preferably efficacious against a broad spectrum of microbes. Specific examples of suitable bactericidal/bacteriostatic agents include, without limitation, POLYMYCIN™, BACITRACIN™, lysozyme, TRICLOSAN™, DOWCIDE™, quaternary amine salts, polyphenols, acid-anionic surfactants, amphoteric surfactant disinfectants, biguanidines, and the like. Specific examples of suitable fungicidal/fungistatic agents include, without limitation, dithiocarbamates, phthalimides, dicarboximides, organophosphates, benzimidazoles, carboxanilides, phenylamides, phosphites, and the like.

Preferably, the microbiological interception enhancing agent is capable of creating a positive charge on the surface of the nanofibers to enhance the electro-kinetic interception of microbiological contaminants. The chemical treatment produces a strong positive charge upon the treated surfaces as measured using streaming or zeta potential analysis and this positive charge is retained at pH values below 10. The cationic material may be a colloid, a small charged molecule or a linear or branched polymer having positively charged atoms along the length of the polymer chain. The cationic material has a counter ion associated therewith. Preferably, the cationic material is water soluble and readily ionizes in an aqueous medium, but has the capacity to be bonded, adsorbed, or incorporated into the surface or bulk of the nanofibers or active agents. The cationic material is present on at least a portion of the surface of the nanofibers or active agents. The microbiological interception enhancing agent further includes a biologically active metal in direct proximity to the cationic material.

If the cationic material is a polymer, the charge density is preferably greater than about 1 charged atom per about every 30 Angstroms, preferably greater than about 1 charged atom per about every 20 Angstroms, and more preferably greater than about 1 charged atom per about every 10 Angstroms of molecular length. The higher the charge density on the cationic material, the higher the concentration of the counter ion associated therewith. A high concentration of an appropriate counter ion can be used to drive the precipitation of the biologically active metal. The high charge density of the cationic material provides the ability to adsorb and significantly reverse the normal negative charge of the nanofibers making it more useful as a microbiological interception enhanced filter medium. The cationic material should consistently provide a highly positively charged surface to the nanofibers as determined by a streaming or zeta potential analyzer, whether in a high or low pH environment.

The use of a cationic polymer of sufficiently high molecular weight allows treatment of the surfaces of the nanofibers without serious attendant impact upon any adsorptive capabilities of the mezo-pores and micro-pores of the carbon or activated carbon immobilized within the integrated paper. The cationic material can have a molecular weight greater than or equal to about 5000 Daltons, preferably greater than or equal to 100,000 Dalton, more preferably greater than or equal to about 400,000 Daltons, and can be greater than or equal to about 5,000,000 Daltons.

The cationic material includes, but is not limited to, quaternized amines, quaternized amides, quaternary ammonium salts, quaternized imides, benzalkonium compounds, biguanides, cationic aminosilicon compounds, cationic cellulose derivatives, cationic starches, quaternized polyglycol amine condensates, quaternized collagen polypeptides, cationic chitin derivatives, cationic guar gum, colloids such as cationic melamine-formaldehyde acid colloids, inorganic treated silica colloids, polyamide-epichlorohydrin resin, cationic acrylamides, polymers and copolymers thereof, combinations thereof, and the like. Charged molecules useful for this application can be small molecules with a single charged unit and capable of being attached to at least a portion of the nanofibers. The cationic material preferably has one or more counter ions associated therewith which, when exposed to a biologically active metal salt solution in an aqueous medium, cause preferential precipitation of a colloidal metal precipitate in direct proximity to the cationic material. The counter ion associated with the cationic material preferentially precipitates with at least a portion of the cation of the biologically active metal salt such that controlled and direct precipitation of a colloidal metal precipitate occurs in proximity to the cationic material. The colloidal metal precipitate, a species comprising of the metal cation and counter ion of the cationic material, is physically trapped within a matrix of the cationic material, or bound to the cationic material either by adsorption, or electrostatic forces.

Exemplary of amines may be pyrroles, epichlorohydrin derived amines, polymers thereof, and the like. Exemplary of amides may be those polyamides disclosed in International Patent Application No. WO 01/07090, and the like. Exemplary of quaternary ammonium salts may be homopolymers of diallyl dimethyl ammonium halide, epichlorohydrin derived polyquaternary amine polymers, quaternary ammonium salts derived from diamines and dihalides such as those disclosed in U.S. Pat. Nos. 2,261,002, 2,271,378, 2,388,614, and 2,454,547, all of which are incorporated by reference, and in International Patent Application No. WO 97/23594, also incorporated by reference, polyhexamethylenedimethylammonium bromide, and the like. The cationic material may be chemically bonded, adsorbed, or crosslinked to the nanofiber and/or to an active particle or fiber captured within the nanofiber material.

Furthermore, other materials suitable for use as the cationic material include BIOSHIELD® available from BioShield Technologies, Inc., Norcross, Ga. BIOSHIELD® is an organosilane product including approximately 5% by weight octadecylaminodimethyltrimethoxysilylpropyl ammonium chloride and less than 3% chloropropyltrimethoxysilane. Another material that may be used is SURFACINE®, available from Surfacine Development Company LLC, Tyngsboro, Mass. SURFACINE® comprises a three-dimensional polymeric network obtained by reacting poly(hexamethylenebiguanide) (PHMB) with 4,4'-methylene-bis-N,N-dilycidylaniline (MBGDA), and a crosslinking agent, to covalently bond the PHMB to a polymeric surface. Silver, in the form of silver iodide, is introduced into the network, and is trapped as submicron-sized particles. The combination is an effective biocide, which may be used in the present invention.

The cationic material when exposed to an aqueous biologically active metal salt solution forms the colloidal metal precipitate that precipitates onto at least a portion of the surface of at least some of the nanofibers and/or active agents. For this purpose, the metals that are biologically active are preferred. Such biologically active metals include, but are not limited to, silver, copper, zinc, cadmium, mercury, antimony, gold, aluminum, platinum, palladium, and combinations thereof. The most preferred biologically active metals are silver and copper. The biologically active metal salt solution is preferably selected such that the metal and the counter ion of the cationic material are substantially insoluble in an aqueous environment to drive precipitation of the colloidal metal precipitate. Preferably, the metal is present in an amount of about 0.01% to about 2.0% by weight of the nanofibers.

A particularly useful microbiological interception enhancing agent is a silver-amine-halide complex. The cationic amine is preferably a homopolymer of diallyl dimethyl ammonium halide having a molecular weight of about 400,000 Daltons or other quaternary ammonium salts having a similar charge density and molecular weight. A homopolymer of diallyl dimethyl ammonium chloride useful in the present invention is commercially available from Nalco Chemical Company of Naperville, Ill., under the tradename MERQUAT® 100. The chloride counter ion may be replaced with a bromide or iodide counter ion. When contacted with a silver nitrate solution, the silver-amine-halide complex precipitates on at least a portion of the nanofibers. Such microbiological interception enhancing agents are taught in co-pending U.S. patent application Ser. No. 10/286,695 filed on Nov. 1, 2002, hereby incorporated by reference in its entirety.

Methods of Making the Integrated Paper of the Present Invention

The integrated paper of the present invention may be made using wet or dry laid processes, as well as other processes known to one of skill in the art. Dry laid processes include spun bonding, electrospinning, spinning islands-in-sea processes, fibrillated films, melt blowing, and other dry laid processes known to one of skill in the art. An exemplary dry laid process starts with staple fibers, which can be separated by carding into individual fibers and are then laid together to a desired thickness by an aerodynamic or hydrodynamic process to form an unbonded fiber sheet. The unbonded fibers can then be subjected to hydraulic jets to both fibrillate and hydroentangle the fibers. Active agents can be incorporated into the precursor paper by dropping the active agents onto the fiber sheet as the nanofibers are laid. A similar process can be performed on certain plastic films that when exposed to high pressure jets of water, are converted into webs of fibrillated fibers. Active agents can be incorporated into the precursor paper by dropping the active agents onto the fiber sheet as the nanofibers are laid.

In a preferred wet laid process, a fiber tow is chopped to a specific length, usually in the range of about 1 millimeter to about 8 millimeters and in particular in the range of about 3 millimeters to about 4 millimeters. The chopped fibers are fibrillated in a device having characteristics similar to a blender, or on a large scale, in machines commonly referred to as a "hi-low", a "beater" or a "refiner". The fiber is subjected to repetitive stresses, while further chopping and the reduction of fiber length is minimized. As the fibers undergo these stresses, the fibers split as a result of weaknesses between amorphous and crystalline regions and the Canadian Standard Freeness (CSF), which is determined by a method well known in the art, begins to decline. Samples of the resulting pulp can be removed at intervals, and the CSF used as an indirect measure of the extent of fibrillation. While the CSF value is slightly responsive to fiber length, it is strongly responsive to the degree of fiber fibrillation. Thus, the CSF, which is a measure of how easily water may be removed from the pulp, is a suitable means of monitoring the degree of fiber fibrillation whenever the fibers have a good tendency to form a wet-laid sheet. However, this is not necessarily the case when handling very stiff fibers such as those made from liquid crystal polymers such as VECTRAN®. If the surface area is very high, then very little water will be drained from the pulp in a given amount of time and the CSF value will become progressively lower as the fibers fibrillate more extensively. Preferably, fibrillation occurs at temperatures greater than about 30° C. to accelerate the process. Enzymes may be added to further accelerate the fibrillation process.

The fibrillated fibers of a given CSF value can be directly used for producing paper or dewatered on a variety of different devices, including a dewatering press or belt, to produce a dewatered pulp. The dewatered pulp can be subsequently used to make a wet-laid paper. Generally, for application in the present invention, a pulp with a CSF of below 100 is used, preferably, the CSF should be less than or equal to about 45, and more preferably less than or equal to about 0. A Canadian Standard Freeness below 0 is achieved when the fibers are fibrillated beyond the time needed to achieve a Canadian Standard Freeness of 0. The fibers can be directly sent to pulp preparation systems to create a furnish suitable for paper making. Functional active agents are slurried with the fibrillated fibers prior to being sent to a paper making machine. To impart anti-microbial properties to the integrated paper, the fibrillated fibers alone or in combination with the active and/or reinforcing agents can be treated with a microbiological interception enhancing agent.

In one preferred embodiment, the nanofibers and/or active agents can be treated with a cationic material in such a manner as to allow the cationic material to coat at least a portion of the surface of at least some of the nanofibers and/or active agents thereby imparting a charge on the nanofibers and/or active agents. Methods of applying the cationic material to the nanofibers and/or active agents are known in the art and include, but are not limited to, spray, dip, or submergence coating to cause adsorption, chemical reaction or crosslinking of the cationic material to the surface of the nanofibers and/or active agents. The treated pulp is then rinsed in reverse osmosis/deionized (RO/DI) water, partially dewatered, usually under vacuum, to produce a wet lap that can then be exposed to a biologically active metal salt solution. The use of nearly ion-free rinse water causes the counter-ions associated with the cationic material to be drawn tightly against the treated surface and to eliminate unwanted ions that may cause uncontrolled precipitation of the biologically active metal into sites remote from the cationic surface.

A metal salt solution is infiltrated into the nanofibers and/or active agents to allow precipitation of the colloidal metal precipitate on a surface of at least a portion of the nanofibers and/or active agents. The precipitation accurately deposits a colloidal metal precipitate adjacent to the cationic coating because the counter-ion associated with this coating reacts with the applied metal salt to form the colloidal particles. After sufficient exposure to the biologically active metal salt solution, the nanofibers can be rinsed and excess water is removed. When silver nitrate is used as the metal salt solution, the presence of precipitated silver can be confirmed by using a Kratos EDX-700/800 X-ray fluorescence spectrometer available from Kratos Analytical, a Shimadzu Group Company, Japan.

Alternatively, once the nanofibers are treated with the microbiological interception enhancing agent, they can be admixed with untreated active and/or reinforcing agents. The fiber mixture can be directly sent to pulp preparation systems to create a furnish suitable for paper making.

Exemplary of a wet laid process includes mixing a pulp of fibrillated lyocell fibers having a Canadian Standard Freeness of about 0 with 5% EST-8 binder fibers, and the active agents to form a slurry in deionized water. A furnish is formed with about 1% to about 2% consistency. It is preferable to add the microbiological interception enhancing agent to the slurry, if anti-microbial properties are desired in the final integrated paper. Next, this pulp is partially dewatered under vacuum and rinsed with deionized water to form a wet lap. Thereafter, the fiber slurry can be directly used in the production of the integrated paper. It is preferable to send the slurry directly into a paper making machine where the economies of scale are easily achieved in making an inexpensive integrated paper for use as a filter medium.

The sheet can also be densified during the paper-making process by passing the precursor paper through a wet press or through the use of a calendar to achieve maximum density in the final product. Heated calendaring of the sheet can produce fiber-fiber and fiber-particle bonds resulting in a densified paper with minimal tendency to shed fibers or particles.

An exemplary dry laid process starts with staple fibers, which can be separated by carding into individual fibers and are then laid together to a desired thickness by an aerodynamic process to form an unbonded fiber sheet. The unbonded fibers can then be subjected to hydraulic jets to both fibrillate and hydroentangle the fibers. A similar process can be performed on certain plastic films that when exposed to high pressure jets of water, are converted into webs of fibrillated fibers. Active agents can be incorporated into the precursor paper by dropping the active agents onto the fiber sheet as the nanofibers are laid. Again, heated calendaring of the sheet can produce a highly densified paper.

An exemplary paper making process uses a furnish with a consistency of up to about 1% by weight in the machine chest. The wet lap moves through the machine at a rate of about 0.1 to about 15 feet/min (about 0.03 to about 4.6 m/min). The press section pressure is about 10 to about 60 psi. Optionally, the paper may be further calendared under heat and pressure to densify the paper. An integrated paper of the present invention having a pore gradient formed from one or more active agents having different densities and settling velocities from each other and/or the nanofibers can be made using paper making processes wherein one or more machine chests are used.

Filtration Devices Utilizing the Integrated Paper

Many types of devices incorporating the integrated paper can be imagined. Described below are certain specific embodiments. However, these devices are exemplary and should not be construed as restricting the scope of the invention.

Gravity-Flow Water Filtration Systems

One embodiment of the integrated paper of the present invention useful in point-of-use gravity-flow water filtration systems includes fibrillated fibers and particles of activated carbon and heavy metal reducing agents. The mean flow path of the activated carbon integrated paper is less than about 2 pm, and preferably less than about 1 pm. The tight pore structure easily allows for mechanical interception of the larger microbiological contaminants such as protozoan cysts. Addition of the microbiological interception enhancing agent aids in electro-kinetic adsorption of smaller particles such as bacteria and viruses. Preferably, this integrated paper is hydrophilic either by using hydrophilic fibers or rendered hydrophilic with agents known in the art that would not foul the pore structure. By adding heavy metal reducing agents such as zeolites, iron oxides, manganese oxide, and the like, the integrated paper provides an inexpensive filter medium that can provide chlorine, taste, odor, lead, and arsenic reduction and microbiological interception. Flow rates can range from about 50 to about 80 ml/minute for a 3 in$^2$ (19.4 cm$^2$) piece of integrated paper. Pleating or folding this type of integrated paper increases the surface area for improved diffusive interception of chemical and microbiological contaminants. The outer layers of the integrated paper protect the inner layers from fouling due to exposure to natural organic matter (NOM) such as humic and fulvic acids.

Pressurized Water Filtration Systems

An integrated paper of the present invention can be used in conjunction with carbon block filtration media well known in the art. Rather than incorporating the active agents in the bulk carbon block where there would be greater axial dispersion due to the dispersion of the active agents through the structure, the active agents are immobilized in the integrated paper and wrapped around or within the interior core of the carbon block. The axial dispersion of the active agents is then collapsed within the integrated paper where the interstitial spaces between the particles of active agents are minimized. Addition of the integrated paper wrap to any carbon block provides inexpensive chemical and microbiological reduction capabilities. Water softening agents such as, for example, zeolites, can be incorporated into the integrated paper for additional functionality. The integrated paper of the present invention can be used in conjunction with a MATRIKX® carbon block filtration media sold by KX Technologies LLC, West Haven, Conn.

Lube Oil Filtration Systems

Engine lube oils must have properties that can effectively prevent corrosion and wear, and often contain additives such as highly basic metallic salts, especially calcium and magnesium salts, as acid neutralizing agents to neutralize the sulfuric acid that is produced as a result of the high sulfur content in certain fuels, especially diesel fuel. A low cost solution would be to incorporate into the lube oil filter paper the additives needed to maintain performance. An integrated paper of the present invention incorporating such additives as acid neutralizing agents such as, but not limited to, magnesium oxide, magnesium hydroxide, calcium or magnesium sulfonates, calcium or magnesium phenates, and the like, can be used alone or in conjunction with an activated carbon filter medium to effectively maintain the performance of the lube oil.

Air Treatment Systems

The integrated paper of the present invention can effectively provide chemical and biological protection in air treatment systems. Preferably, the integrated paper has immobilized therein activated carbon, in particular an impregnated carbon such as, for example, ASZM-TEDA carbon, zeolites, metal impregnated minerals, other specialized materials such as copper or calcium sulfates or sulphonates, silver oxide, and combinations thereof. Such air treatment systems can include filtration media incorporating the integrated paper into pleated panels, with or without a supporting substrate, for building HVAC systems; respirators; and collective protection applications in shelters, armored fighting vehicles or any other closed space.

EXAMPLES

The following examples are provided to illustrate the present invention and should not be construed as limiting the scope of the invention.

Hand sheets of the integrated papers in the following examples were made with fibrillated nanofibers using the following general method. Materials were weighed out and blended with 2.0 L deionized water for at least 5 minutes in a stainless steel Waring blender. The deionized water may be heated to temperatures greater than about 30° C. When non-lyocell fibers were used, they were blended separately for about 3 minutes prior to mixing with any fibrillated lyocell nanofibers. Functional active or reinforcing agents were periodically slurried and blended with the fiber mixture. The fiber mixture was poured into a 30.5×30.5 $cm^2$ stainless steel FORMAX™ paper making deckle with a sheet of REEMAY™ 2004 nonwoven laid over the 100 mesh base screen as a support layer. The deckle was filled to a total of about 12 L of water containing the various fibers and functional active or reinforcing agents. A 30.5×30.5 $cm^2$ stainless steel agitator plate having 60 holes of 2 cm diameter was used to plunge the ingredients up and down from top to bottom about 8 to 10 times. The water was removed from the fiber mixture by pulling a slight vacuum below the deckle to cause the fibers to form on the REEMAY™ nonwoven. Once the bulk of the water is removed, supplemental dewatering is accomplished with a vacuum pump to remove additional excess moisture and to create a relatively smooth, flat, fairly thin paper-like sheet. The resulting sheet is separated from the screen and combined with a blotter sheet on both top and bottom. The combination of sheets is gently rolled with a 2.27 kg marble rolling pin to remove excess water and smooth out the top surface of the sheet. The sheet is then placed between two fresh and dry blotter sheets and placed on a FORMAX® sheet dryer for about 10 to about 15 minutes at about 120° C. The REEMAY™ nonwoven sheet is separated and discarded at this point. Commercial manufacture of the precursor paper can be accomplished on a Fournier wire, rotoformer, or similar systems.

Examples 1 to 4

Integrated Silver Oxide Paper of the Present Invention

Multiple sheets of silver oxide ($Ag_2O$) paper were made according to the procedure described above using lyocell nanofibers having a Canadian Standard Freeness of less than about 0 ("CSF-X" fiber). The highly loaded, integrated silver oxide paper is useful in absorbing carbon dioxide for applications such as, but not limited to, respirators and other air treatment apparatus. Proportions of the nanofibers, dry weight, and silver oxide are outlined in Table I. All of these papers allowed the silver oxide to adsorb carbon oxide forming silver carbonate, and could be regenerated by heating back to silver oxide for further adsorption. The nanofibers easily held the roughly 10 micron silver oxide particles.

TABLE I

| | Ex # | | | |
|---|---|---|---|---|
| | 1 | 2 | 3 | 4 |
| $Ag_2O$ | 60.0 g | 60.0 g | 60.0 g | 319.2 g |
| CSF-X | 6.0 g | 3.0 g | 3.0 g | 16.8 g |

Examples 5 to 8

Integrated Carbon Paper of the Present Invention

An integrated paper was made according to the procedure described above with the addition of carbon and amorphous titanium silicate (ATS) to aid in the adsorption of lead and chlorine with a mean pore size between 0.5 to 0.7 microns to promote bacterial filtration. Paper ingredients were fibrillated lyocell fibers having a Canadian Standard Freeness of about 0; bituminous coal based carbon ground to a particle size of 85×325 mesh with 28% by weight −325 mesh powder; glass microfibers from Johns Mansville Company, Denver, Colo., under the trade designation FIBREGLASS™ #106; ATS from Engelhard Corporation, Iselin, N.J.; and SHORT STUFF® EST-8 polyethylene fibers commercially available from MiniFibers, Inc., Pittsburgh, Pa. Proportions in dry weight of the integrated carbon papers are shown in Table II below. All examples produced papers having a mean pore size between 0.5 to 0.7 microns sufficient to filter out bacterial contaminants, as well as protozoan cysts.

TABLE II

|  | Ex # | | | |
| --- | --- | --- | --- | --- |
|  | 5 | 6 | 7 | 8* |
| CSF 0 | 10.50 g | 9.45 g | 3.50 g | 10.50 g |
| ATS | 7.00 g | 7.00 g | 7.00 g | 7.00 g |
| EST-8 | 3.50 g | 2.80 g | 2.10 g | 2.80 g |
| Glass | 1.75 g | 3.50 g | 10.20 g | 2.45 g |
| Carbon | 12.25 g | 12.30 g | 12.25 g | 12.30 g |

*Ingredients cast on tea bag paper and later removed.

The paper of Example 8 was further tested for its ability to remove lead. A 3.25 inch (8.26 cm) diameter disc of the paper was fitted into a housing with a head pressure of 5 inches (12.7 cm) and challenged with 3 gallons of water having a lead content of 150 ppb lead at a pH of about 9. The integrated paper of the present invention as embodied in Example 8 was able to reduce the lead concentration to below 10 ppb lead, and in some cases undetectable levels, at flow rates of about 28 to 32 ml/minutes.

Example 9

Integrated Magnesium Hydroxide Paper of the Present Invention

An integrated paper was made in accordance with the procedure described above with 8.8 g of fibrillated lyocell fibers having a Canadian Standard Freeness of about 23, 91.3 g magnesium hydroxide, 6.6 g of SHORT STUFF® EST-8 polyethylene fibers, and 3.3 g abaca fibers. The resultant paper had a basis weight of 104.25 g/ft$^2$, a thickness of 1.53 millimeters. The mean pore diameter of the integrated magnesium hydroxide paper is less than about 1 micron. The magnesium hydroxide paper is suitable for controlling acidity in lube oils.

The integrated paper of the present invention provides an economical filter medium useful in removing microbiological and chemical contaminants. The paper can be made using paper-making processes for speed and efficiency. Active particles immobilized therein provide functionality to the integrated paper for applications such as adsorption of carbon dioxide with silver oxide in air filtration; controlling acidity in lube oil with magnesium hydroxide/oxide; combinations of activated carbon, a lead reduction zeolite, and/or an arsenic to provide an inexpensive cyst-reducing water filtration medium that also intercepts lead, chlorine, and odors while improving taste; and immobilizing titanium dioxide for the production of photocatalytic membranes.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A method of immobilizing particles comprising the following steps in the sequence set forth:
    providing fibers;
    fibrillating said fibers at a temperature greater than about 30° C. to form fibrillated fibers having an average fiber diameter of less than about 1000 nm;
    providing a plurality of active agents wherein an average diameter of said fibrillated fibers is less than an average particle size of said active agents;
    treating at least a portion of at least some of said fibrillated fibers and/or said active agents with a microbiological interception enhancing agent, said microbiological interception enhancing agent comprising a colloidal metal-cationic complex of a biologically active metal precipitated with a counter ion of a cationic material residing on said at least portion of said at least some of said fibrillated fibers and/or said active agents whereby the colloidal metal precipitates adjacent to the cationic material;
    admixing together said fibrillated fibers and said active agent;
    immobilizing said microbiological interception enhancing agent treated admixed fibrillated fibers and active agent into an integrated paper having a mean flow path of less than about 2 µm whereby said immobilized fibrillated fibers, active agents and microbiological interception enhancing agent reside within and throughout an entire thickness of said integrated paper.

2. The method of claim 1 wherein said microbiological interception enhancing agent is formed only on said fibrillated fibers.

3. The method of claim 1 wherein said microbiological interception enhancing agent is formed only on said active agents.

4. The method of claim 1 wherein said microbiological interception enhancing agent is formed on both said fibrillated fibers and said active agents.

5. The method of claim 1 wherein said fibrillated fibers or said active agents are treated with said microbiological interception enhancing agent prior to admixing together.

6. The method of claim 1 wherein said fibrillated fibers or said active agents are treated with said microbiological interception enhancing agent subsequent to admixing together.

7. The method of claim 1 further comprising the steps of forming said microbiological interception enhancing agent in the sequence set forth comprising:
    coating said at least portion of at least some of said fibrillated fibers and/or said active agents with said cationic material;
    rinsing said coated fibrillated fibers and/or said active agents with a nearly ion-free rinse water;
    exposing said rinsed, coated fibrillated fibers and/or said active agents to a biologically active metal salt solution, such that, said biologically active metal precipitates with said counter ion of said cationic material to form said colloidal metal precipitate adjacent to the cationic material, said nearly ion-free rinse water enabling said counter ion to be drawn tightly against said coated fibrillated fibers and/or said active agents and eliminating unwanted ions that cause uncontrolled precipitation of the biologically active metal into sites remote from said cationic material.

8. The method of claim 1 wherein said fibrillate fibers comprise hydroentangled fibrillated fibers immobilized within said integrated paper.

9. The method of claim 1 wherein said fibrillate fibers physical entrapment of said active agents within said integrated paper due to said fibrillated fibers having said average fiber diameter less than said average particle size of said active agents.

10. The method of claim 1 wherein said plurality of active agents are selected from the group consisting of metals, metal salts, metal oxides, alumina, carbon, activated carbon, silicates, ceramics, zeolites, diatomaceous earth, activated bauxite, fuller's earth, calcium sulfate, titanium dioxide, magnesia, magnesium hydroxide, magnesium oxide, manganese oxides, iron oxides, perlite, talc, clay, bone char, calcium hydroxide, calcium salts, or combinations thereof.

11. The method of claim 1 wherein said fibrillated fibers and said active agents have different settling velocities such that said fibrillated fibers settle to one surface of the integrated paper and the active agents settle to the other surface of the integrated paper so that an asymmetric pore gradient exists through the thickness of the integrated paper.

12. The method of claim 1 wherein said asymmetric pore gradient provides an integrated paper having a pore structure from a prefiltration structure to a final polishing filter.

13. The method of claim 1 wherein the active agents are present in an amount of up to about 50 weight percent based on a total weight of the integrated paper.

14. The method of claim 1 wherein the active agents are present in an amount of up to about 75 weight percent based on the total weight of the integrated paper.

15. The method of claim 1 wherein the active agents are present in an amount of up to about 95 weight percent based on the total weight of the integrated paper.

16. The method of claim 1 further including binder fibers or particles having an average diameter equal to or less than the average particle size of the active agents to physically entrap the active agents within the integrated paper.

17. The method of claim 1 wherein said integrated paper has a mean pore size of less than or equal to about 1 micron to provide supplemental direct mechanical interception of microbiological contaminants in combination with the microbiological interception enhancing agent.

18. The method of claim 14 wherein said fibrillated fibers have an average diameter of less than or equal to 250 nm.

19. A method of immobilizing particles comprising the following steps in the sequence set forth:
   providing fibrillating fibers;
   providing a plurality of active agents wherein an average diameter of said fibrillated fibers is less than an average particle size of said active agents;
   providing a cationic material on at least portions of at least some of said fibrillated fibers and/or said active agents, said portions having a counter ion of said cationic material;
   forming a microbiological interception enhancing agent comprising a metal-cationic complex by treating said at least portions of at least some of said fibrillated fibers and/or said active agents with a biologically active metal solution to precipitate said biologically active metal with said counter ion of said cationic material;
   admixing together said treated fibrillated fibers and said treated active agents;
   immobilizing said fibrillated fibers, active agents and microbiological interception enhancing agent into an integrated paper.

20. A method of immobilizing particles comprising the following steps in the sequence set forth:
   providing a plurality of fibrillating fibers;
   providing a plurality of active agents wherein an average diameter of said fibrillated fibers is less than an average particle size of said active agents;
   providing a cationic material on at least portions of at least some of said fibrillated fibers and/or said active agents, said portions having a counter ion of said cationic material;
   forming a microbiological interception enhancing agent comprising a metal-cationic complex by treating said at least portions of at least some of said fibrillated fibers and/or said active agents with a biologically active metal solution to precipitate said biologically active metal with said counter ion of said cationic material;
   admixing together said treated fibrillated fibers and said treated active agents;
   immobilizing said treated admixed fibrillated fibers and active agent into an integrated paper, whereby said fibrillated fibers hydroentangle within said integrated paper to physical entrap said active agents and said microbiological interception enhancing agent within and throughout an entire thickness of said integrated paper.

21. The method of claim 20 wherein said metal-cationic complex is a colloidal metal precipitate of a silver-amine-halide complex.

22. The method of claim 20 wherein said integrated paper has a mean flow path of less than about 2 μm.

23. The method of claim 20 wherein said microbiological interception enhancing agent is formed on both said fibrillated fibers and said active agents.

24. The method of claim 20 wherein said fibrillated fibers and said active agents have different settling velocities such that said fibrillated fibers settle to one surface of the integrated paper and the active agents settle to the other surface of the integrated paper so that an asymmetric pore gradient exists through the thickness of the integrated paper.

25. The method of claim 20 wherein said integrated paper has a mean pore size of less than or equal to about 1 micron to provide supplemental direct mechanical interception of microbiological contaminants in combination with the microbiological interception enhancing agent.

\* \* \* \* \*